(12) United States Patent
George

(10) Patent No.: US 11,433,093 B2
(45) Date of Patent: Sep. 6, 2022

(54) COMPACT GYROPLANE EMPLOYING TORQUE COMPENSATED MAIN ROTOR AND HYBRID POWER TRAIN

(71) Applicant: John Stevens George, Abiquiu, NM (US)

(72) Inventor: John Stevens George, Abiquiu, NM (US)

( * ) Notice: Subject to any disclaimer, the term of this patent is extended or adjusted under 35 U.S.C. 154(b) by 236 days.

(21) Appl. No.: 16/528,672

(22) Filed: Aug. 1, 2019

(65) Prior Publication Data

US 2021/0030784 A1 Feb. 4, 2021

(51) Int. Cl.
| | |
|---|---|
| *B64C 27/02* | (2006.01) |
| *B64C 27/24* | (2006.01) |
| *B64D 27/00* | (2006.01) |
| *A61K 31/728* | (2006.01) |
| *C12N 7/00* | (2006.01) |
| *A61K 31/7105* | (2006.01) |
| *C12N 15/86* | (2006.01) |
| *A61K 9/14* | (2006.01) |
| *A61K 48/00* | (2006.01) |
| *B64D 27/24* | (2006.01) |
| *B82Y 5/00* | (2011.01) |
| *B64D 27/02* | (2006.01) |

(52) U.S. Cl.
CPC ............ *A61K 31/728* (2013.01); *A61K 9/141* (2013.01); *A61K 31/7105* (2013.01); *A61K 48/0041* (2013.01); *B64C 27/02* (2013.01); *B64C 27/025* (2013.01); *B64D 27/24* (2013.01); *C12N 7/00* (2013.01); *C12N 15/86* (2013.01); *B64D 2027/026* (2013.01); *B82Y 5/00* (2013.01); *C12N 2310/141* (2013.01); *C12N 2710/00042* (2013.01); *C12N 2710/10042* (2013.01)

(58) Field of Classification Search
CPC ..... B64C 27/02; B64C 27/022; B64C 27/025; B64C 27/10; B64C 27/24; B64C 27/52; B64C 2027/026
USPC ....................................................... 244/17.11
See application file for complete search history.

(56) References Cited

U.S. PATENT DOCUMENTS

| | | | | |
|---|---|---|---|---|
| 3,174,708 A | * | 3/1965 | Miles ..................... | B64C 27/025 244/17.25 |
| 4,589,611 A | * | 5/1986 | Ramme .................... | B64C 27/10 244/12.3 |
| 4,730,795 A | * | 3/1988 | David ...................... | B64C 27/22 244/17.21 |
| 4,913,376 A | * | 4/1990 | Black ...................... | B64C 27/02 244/17.11 |
| 5,791,592 A | * | 8/1998 | Nolan ..................... | B64C 27/14 244/17.11 |

(Continued)

*Primary Examiner* — Joshua E Rodden

(57) ABSTRACT

A gyroplane employing torque compensated main rotor and hybrid power train is disclosed. The invention incorporates a torque-compensated main rotor system with a common Collective pitch control, which can be driven transiently during flight to allow Vertical Take-Off, Landing and Hovering (VTOLH) flight operations. Torque compensation is via a coaxial counter-rotating (CACR) rotor system, or alternatively using a single rotor in conjunction with one or more electronically-controlled, fixed-pitch, thruster motors. The use of electric motors for lift and torque compensation facilitates electronic and potentially autonomous control of all phases of vertical flight.

11 Claims, 3 Drawing Sheets

(56) References Cited

U.S. PATENT DOCUMENTS

| | | | | |
|---|---|---|---|---|
| 6,062,508 A * | 5/2000 | Black | | B64C 37/00 |
| | | | | 244/17.11 |
| 6,086,016 A * | 7/2000 | Meek | | B64C 27/02 |
| | | | | 244/17.11 |
| 6,886,777 B2 * | 5/2005 | Rock | | B64C 27/10 |
| | | | | 244/17.23 |
| 7,448,571 B1 * | 11/2008 | Carter, Jr. | | B64C 27/02 |
| | | | | 244/17.11 |
| 7,677,492 B1 * | 3/2010 | Carter, Jr. | | B64C 27/022 |
| | | | | 244/17.11 |
| 8,584,983 B2 * | 11/2013 | Sirohi | | B64C 27/10 |
| | | | | 244/17.27 |
| 8,876,057 B2 * | 11/2014 | Alber | | B64C 39/024 |
| | | | | 244/137.1 |
| 8,960,594 B2 * | 2/2015 | Groen | | B64C 27/18 |
| | | | | 244/17.11 |
| 9,145,831 B1 * | 9/2015 | White | | F02K 7/005 |
| 9,561,850 B2 * | 2/2017 | Tsunekawa | | B64C 29/0033 |
| 10,370,094 B2 * | 8/2019 | Garcia | | B64C 27/10 |
| 10,494,095 B2 * | 12/2019 | Groninga | | B64C 27/82 |
| 10,843,794 B2 * | 11/2020 | Nguyen | | B64C 27/26 |
| 10,858,096 B1 * | 12/2020 | Schmaling | | B64C 27/48 |
| 2006/0269413 A1 * | 11/2006 | Cotton | | B64C 27/82 |
| | | | | 416/170 R |
| 2010/0001120 A1 * | 1/2010 | Sun | | B64C 27/26 |
| | | | | 244/6 |
| 2012/0168556 A1 * | 7/2012 | Sonneborn | | B64C 27/18 |
| | | | | 244/17.23 |
| 2012/0199692 A1 * | 8/2012 | van der Westhuizen | | |
| | | | | B64C 27/26 |
| | | | | 244/17.25 |
| 2013/0037652 A1 * | 2/2013 | van der Westhuizen | | |
| | | | | B64C 27/027 |
| | | | | 244/17.11 |
| 2014/0246538 A1 * | 9/2014 | Morris | | B64C 19/00 |
| | | | | 244/17.13 |
| 2017/0066539 A1 * | 3/2017 | van der Westhuizen | | |
| | | | | B64C 27/18 |
| 2017/0158354 A1 * | 6/2017 | Bourne | | B64C 39/024 |

* cited by examiner

COMPACT GYROPLANE EMPLOYING TORQUE COMPENSATED MAIN ROTOR AND HYBRID POWER TRAIN

CROSS REFERENCE TO RELATED APPLICATIONS

Provisional Patent Application 62/712,485, filed Jul. 31, 2018.

REFERENCES (US PATENTS)

V. Bendix. Helicopter with Coaxial Rotors. U.S. Pat. No. 2,456,485, December 1948.

R. R. Bergquist et al. Coaxial Rigid Rotor Helicopter and Method of Flying Same. U.S. Pat. No. 3,409,249 November 1968.

V. Mendiberri. Helicopter of the Type Having Two Coaxial Counter-rotating Rotors with a drive Mechanism Interposed between the Power Plant and the Rotors. U.S. Pat. No. 4,216,925, August 1980.

I. B. Benson. Autogyro with Auxilliary Rotor Drive. U.S. Pat. No. 4,653,705 March 1987.

F. E. Black. VTLH Autogyro. U.S. Pat. No. 491,337, April 1990.

R. Leon. Ultralight Helicopter and Control System. U.S. Pat. No. 5,370,341, December 1994.

Groen et al. Autogyro Aircraft. U.S. Pat. No. 5,304,036, April 1994.

F. E Black, Compound Aircraft. U.S. Pat. No. 6,062,508, April 2000.

B. Holbien. Counter rotating Circular wing for Aircraft, U.S. Pat. No. 6,450,446 B1, September 2002.

J. Carter Jr. Hovering Gyro Aircraft. U.S. Pat. No. 6,513,752 B2. February 2003.

L. R. Neal. Fly-drive Vehicle. U.S. Pat. No. 6,978,969 B1, December 2005.

Phelps III et al. Ultralight Coaxial Rotor Aircraft. U.S. Pat. No. 7,198,223 B2 April 2007.

BACKGROUND OF THE INVENTION

Problem Solved

We describe a compact personal aircraft based on a gyroplane, with capabilities for vertical takeoff and landing, and hovering, that is safer, simpler, less expensive, and mechanically less complex than existing helicopters.

Conventional light helicopters employ a fixed, driven main rotor with a Collective function to modulate lift and a Cyclic function for directional control, and a mechanically-coupled, variable-pitch tail rotor to compensate for the effects of torque. These systems allow helicopters to take off and land vertically or hover in place, but also contribute to mechanical complexity, significant expense of acquisition and maintenance, and substantial demands on the pilot in normal and emergency operations.

Conventional gyroplanes employ a freely turning main rotor operating in autorotation, a simple gimballed, teetering rotor head for pitch and directional control, and a tail assembly analogous to a fixed wing aircraft for yaw control and pitch stabilization. Forward propulsion is accomplished with a propeller, typically in a pusher configuration. Modern gyroplanes often employ "prerotation" of the rotor, reducing the distance required to achieve rotor flight speed in a conventional rolling takeoff.

This invention employs the general configuration of a gyroplane, adding a torque-compensated main rotor system with a common Collective pitch control which can be driven during flight to allow Vertical TakeOff, Landing and Hovering (VTOLH) flight operations. Torque compensation is via a coaxial counter-rotating (CACR) rotor system, or alternatively using a single rotor together with one or more electronically-controlled and driven thruster motors. A hybrid mechanical, hydraulic or electro-mechanical power system allows use of a single engine or multiple power sources to power vertical lift and forward propulsion; the use of electric motors for lift and torque compensation facilitates electronic (and potentially autonomous) control of critical phases of flight.

PRIOR ART

The Gyroplane is the predecessor to the modern helicopter and is the source of a number of technical innovations that contributed to the ultimate success of the helicopter. However, the unique capabilities of the helicopter for vertical flight, eclipsed the advantages of gyroplanes and delayed their development for decades.

Helicopters can take off and land vertically or hover in place if adequate power is available under the conditions of flight. By changing the pitch of the main rotor blades, it is possible to make fine adjustments to the lift provided by the machine. By adjusting the pitch of the tail rotor, it is possible to null out precisely the effects of torque that are an inherent challenge of a single rotor design, or to yaw the craft from side to side or even to spin in place. By cyclically varying the pitch of each rotor blade as it completes its circuit of the rotor disk, it is possible to drive the helicopter forward or backward or to roll along any arbitrary axis.

The clever designs that provide the functional versatility of a helicopter with only a single power-plant and a pair of rotors, entail considerable mechanical and operational complexity. The mechanical complexity contributes to the very substantial costs of production and maintenance of a conventional helicopter. It also means that a failure in any one of dozens of interconnected systems can render the aircraft difficult to control or even incapable of flight.

Even when the helicopter is operating entirely as it should, the demands on the pilot are great. The range of motion of the primary flight controls required for adequate aircraft control over the entire flight envelope are much greater that the minute adjustments required in stabile flight, so that considerable practice and experience are required for proficient operation. Compounding this problem is the fact that (to first order) every control system interacts with every other. The addition of systems to automate basic control processes such as throttle or rotor RPM can greatly reduce pilot workload in normal operations. Nevertheless, in a typical modern helicopter an emergency such as a loss of power requires an immediate and decisive response to lower the collective, in order to preserve the rotational speed of the rotor and prevent an unrecoverable blade stall. The ensuing autorotation requires a steep descent, properly arrested at the last moment to avoid damage to the aircraft or its passengers.

Many of the issues that plague helicopters are avoided (or at least mitigated) in the autogyro or gyroplane, the predecessor to the modern helicopter. The gyroplane is a rotor-craft, developed in the early 1920s by the Spaniard, Juan de la Cierva. Design objectives included enhanced lift at low speed, and elimination of the risk of stall. Early autogyros were essentially airplanes to which a mast and rotor were added. Takeoff was accomplished by rolling down a runway until adequate rotor speed and lift was achieved for liftoff. Unfortunately, the rotor added significant induced and parasitic drag so a long runway was required. De la Cierva introduced a number of ideas that proved crucial for subsequent successful rotorcraft, most importantly the use of a hinged or "teetering" rotor, which allows the rotor to self-adjust in flight to balance the requirements for lift with differences in speed of the advancing and retreating blades during take-off roll or horizontal flight, i.e. the so-called "dissymmetry of lift."

In the gyroplane, like the helicopter, the fuselage that carries passengers, mechanical and control systems, engine and fuel, hangs from a spinning disk that provides lift. But the rotor in a conventional gyroplane is not driven directly by the engine. Instead, a propeller drives the craft forward, and air steaming upward through the disk produces autorotation of the rotor blades that in turn produces lift. In forward flight the gyroplane always operates in autorotation; the loss of forward thrust does not require abrupt changes in the control configuration of the aircraft. The pilot simply decides where to land (which may be directly below) and executes a relatively normal approach to landing. With reasonable skill, even the last few feet may be effectively vertical, with little or no roll-out after landing.

The typical gyroplane is much simpler mechanically than the helicopter. In a conventional gyroplane each rotor blade is held at a fixed pitch. There is no collective or cyclic control to allow the pilot to adjust rotor pitch. Instead the rotor assembly is typically mounted on a gimbal that allows the entire plane of the rotor disk to be adjusted fore to aft or side to side. The rotor assembly is typically attached by a pair of pushrods or cable-based actuators to the control stick, which operates with a control logic analogous to that of an airplane. Alternatively, in simple rotorcraft, it is possible to change the attitude of the rotor disk directly with a T-bar or similar structure, analogous to the control of a hang glider or weight-shift ultralight. Indeed, investigation of the prior art discloses examples of a Benson "gyrocopter" with T-bar controls as well as a patent for an ultralight helicopter controlled by weight shift.

Because the gyroplane rotor is not powered, there is no need to compensate for the torque inherently present in a single rotor helicopter. In a gyroplane in forward flight there is no need for a tail rotor; tail control surfaces analogous to those on a fixed wing airplane, consisting of a vertical stabilizer and rudder (and optionally, but usefully, a horizontal stabilizer) provide adequate control authority.

In some simple gyroplanes including many early Benson gyrocopters the rotor was spun by hand. Most modern gyroplanes use some form of prerotation to achieve higher rotor RPM before the takeoff roll is initiated. Patents by Benson and others describe such a system. A range of mechanical systems are employed to spin up the main rotor including rigid shafts (with a universal or constant velocity joint to accommodate the teetering rotor), enclosed rotating cables, or hydraulic systems. These systems typically borrow power from the prime mover that drives the gyroplane in forward flight. Recently electric prerotation systems have appeared. Given the pattern of use in a gyroplane and rapid advances in motor and battery technology, these are an attractive option.

Even with prerotation, significant ground runs are required for takeoff in a conventional gyroplane, though in strong enough winds it is sometimes possible to lift off more or less vertically. Power must be removed before takeoff; otherwise fuselage yaw or spinning due to torque is observed. Prerotating to higher speeds in a fixed pitch gyroplane typically is not practical because of the power required to drive a main rotor. Even if adequate power is available, prerotation up to flying speed is likely to result in a prolonged transition through a zone of instability when lift is approximately equal to that required for lift-off. Even if prerotation is disengaged before that point, drag initially reduces rotor speed when forward motion is achieved.

Nevertheless, it is possible to achieve routine vertical takeoff in a gyroplane. So-called "jump" takeoffs were explored by the pioneers of autogyro flight, including de la Cierva, and his successor Pitcairn, and have been demonstrated in the modern era by a number of developers. Notably, Degraw and Boyette achieved this milestone in response to a challenge over 25 years ago. Others including the commercial entity Carter Copters have employed similar strategies with similar results.

The general strategy is to outfit the autogyro with a mechanism for adjusting rotor pitch, analogous to the collective function of a conventional helicopter. Prerotation is initiated with the rotors at neutral or negative pitch, and proceeds to ~150% of the fixed pitch lift-off RPM. Then the mechanism for prerotation is disengaged, and the pitch is adjusted for flight. In order to gain altitude aggressively and preserve rotor momentum for long enough to achieve forward flight, the takeoff tends to be rather ballistic. The transition is often associated with a yawing or rolling moment. If forward motion is not established quickly, the craft will rapidly settle in autorotation. Although jump take-off gyroplanes address the most significant deficit of the autogyro relative to the helicopter, to date they have not achieved widespread use nor significant commercial success.

Once the autogyro was endowed with a mechanism to allow Collective control of the pitch of the rotor blades as required for a jump takeoff, the development of a mechanism (employing an intermediate "swash plate") to rapidly change the pitch of the individual blades over the course of each cycle or circuit of the rotor, soon followed. This Cyclic function, originally developed for the Pitcairn gyroplane, was a key enabling technology for the development of the modern helicopter, allowing the driven rotor to spin in a fixed plane while allowing control the effective pitch of the rotor disk. This strategy can mitigate issues such as stick shake, associated with physically tilting a gyroscopic disk, e.g. in a gimballed single rotor helicopter. The comparative simplicity of a gimballed rotor head with teetering rotor has led to its almost universal use in modern light gyroplanes. However, a fixed disk rotor with collective and cyclic controls as used in light helicopters, can descend without power in autorotation, and there are examples of gyroplanes (e.g. the Air and Space 18a) which fly in autorotation using a fixed-disk, fully articulated rotor system with collective and cyclic functions, functionally equivalent to those in helicopters.

The present invention is motivated by a desire to take advantage of the significantly lower costs of gyroplane flight, enjoying the safety and operational simplicity afforded by flight in autorotation, while achieving capability for benign vertical take-off, landing and hovering.

The proposed rotor system employs variable pitch to allow efficient prerotation while allowing a crisp transition to vertical flight.

An electronically driven and controlled "tail rotor" can compensate for the torque produced by a single driven main rotor. Alternatively, a pair of thrusters on suitable arms or wings would allow torque compensation and could serve double duty, providing propulsion for forward flight. Either system can enable the ability to apply power to the gyroplane rotor system during flight.

A preferred embodiment of this invention uses a main rotor system with coaxial counter-rotating rotors to effectively cancel torque. The idea of a single coaxial rotor pair was considered in early designs by many of the pioneers in rotorcraft flight and was successfully demonstrated in a 1933 helicopter design by Breguet, as well as others. The design creates topological difficulties and mechanical complexity for the traditional Collective and Cyclic functions, but the problem can be solved, e.g. in the Russian Kamov helicopters. A gimballed rotor head as commonly used on gyroplanes could significantly simplify the control systems in the CACR rotor assembly, eliminating the need for a Cyclic control. Of course, for reasons previously discussed, a collective function remains very useful or essential for control of vertical takeoff and flight.

We are unaware of any example of the use of a CACR rotor system in a conventional gyroplane. We have seen at least one example of a very simple RC gyroplane with counter-rotating rotors, which are unlinked and spin up passively in forward motion. Looking for prior art in the patent literature we find two patents of particular interest. A 1990 patent by Black describes a novel gyroplane incorporating a coaxial, counter-rotating rotor system, employing small peripheral rotor blades attached to a lifting disk. Although a model exists, a full-scale version has never been built. A patent by Holbein describes a similar concept, intended to operate without individual rotor blades.

A series of patents by Norris and colleagues lay the basis for a light helicopter dubbed the AirScooter. The patent describes a design for a CACR main rotor system. incorporating a relatively simple mechanical design with bevel gears or a planetary gear system to precisely synchronize rotation. The patented design did not include capability for either cyclic or collective control. The effects of cyclic control were achieved with a gimballed rotor assembly, as in a conventional gyroplane. Liftoff was achieved by varying engine speed. A series of models and several prototype aircraft were produced and flown. Ultimately, the project was abandoned because of significant cost overruns in the development of a suitable engine. This problem was exacerbated by the fact that without a collective, the helicopter could not be configured to descend in autorotation in the event of an engine failure.

DETAILED DESCRIPTION OF THE INVENTION

Figure 1:
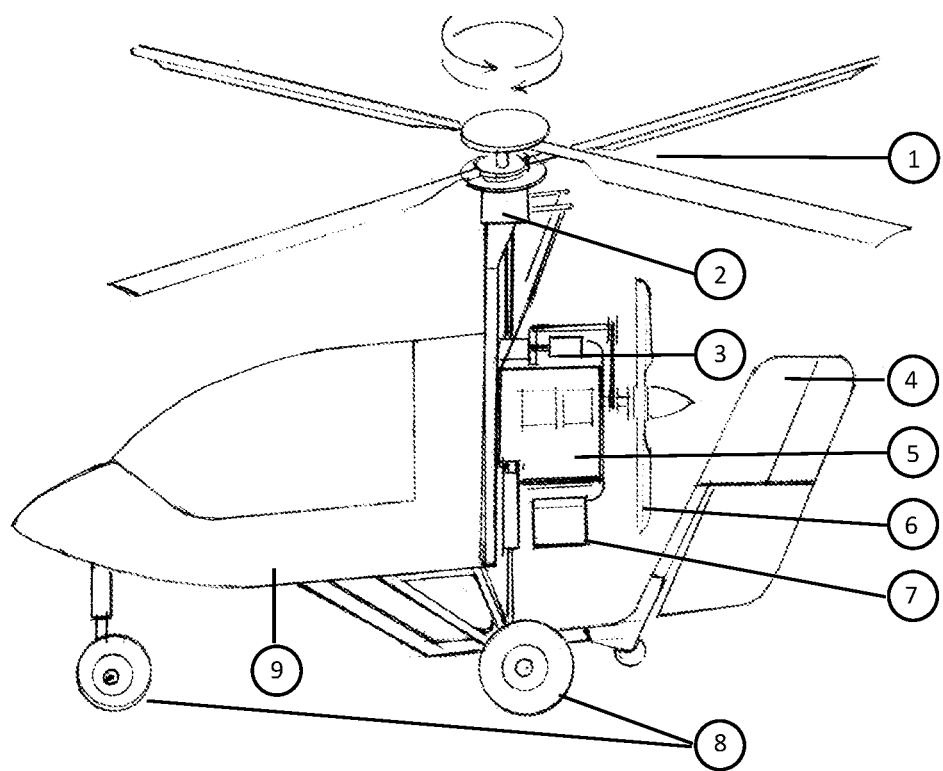
FIG. 1 is a perspective view of the VTOL Gyroplane.

We describe a compact personal aircraft with capabilities for vertical takeoff and landing, and hovering, that is safer, simpler, and mechanically less complex than existing helicopters. The invention claimed here solves this problem.

We propose a compact aircraft based on the general configuration of a gyroplane, with a propeller for propulsion, and a transiently driven, torque-compensated main rotor system which incorporates degrees of freedom to allow the system to self-adjust for aerodynamic forces. Collective adjustment of pitch is employed to allow control of lift. A Gimballed main rotor can be employed for directional control, instead of the more complex Cyclic control function used by helicopters. Torque compensation is by a coaxial counter-rotating (CACR) rotor system, or alternatively using a conventional "Teetering" rotor paired with one or more electronically controlled and electrically driven thruster motors. The aircraft employs a hybrid power train to enable long range, continuous operation. An Internal Combustion Engine (ICE) can be employed to drive the propeller for horizontal propulsion in cruise; during takeoff and landing the main rotor system is driven transiently by the engine via mechanical or hydraulic linkage, or in a preferred embodiment, by one or more electric motor(s). The electric drive system incorporates a battery and power supply system sufficient for full power operation throughout transient phases of flight (vertical take-off, landing and hovering (VTOLH)), recharging the battery during cruise flight using excess power of the ICE. The use of electric motors facilitates electronic control of function during critical phases of flight. These teachings enable VTOLH gyroplanes with the inherent safety advantages due to cruise operation in autorotation. Derivative designs may produce aircraft with capabilities for relatively seamless transition to high-performance land operations on and off-road, on skis, and/or service as an amphibious, fan-driven hydroplane.

The claimed invention differs from and is an improvement on what currently exists. The invention combines the key functional capabilities of a conventional helicopter for vertical take-off, landing, and hovering, with the advantages of a modern gyroplane, including reduced mechanical complexity, reduced costs of acquisition and maintenance, lower demands on pilot skill and workload, and enhanced safety.

The mechanical complexity of conventional helicopters contributes to their substantial acquisition and maintenance costs, and introduces multiple potential sources of single point failures. The requirement for proper and coordinated control responses during normal operation, and especially during emergencies contributes to overall operational complexity and required high levels of pilot skill. Conventional gyroplanes are much simpler and less demanding, but are comparatively limited in capability for vertical flight; jump gyroplanes can achieve vertical liftoff but introduce additional mechanical and operational complexity.

A mechanical or electro-mechanical hybrid power system allows a single engine to power vertical lift and forward propulsion; the use of electric motors for lift and torque compensation facilitates electronic (and potentially autonomous) control of critical phases of flight, and provides a redundant fail-safe power system.

FIG. 1: General Configuration of VTOL Gyroplane:

The subject invention incorporates key components of a conventional gyroplane including airframe and fuselage, landing gear, an engine and propeller to provide forward thrust, and a main rotor system operating in autorotation, employing a gimballed rotor head for directional control. To this platform is added a torque compensated main rotor system and a hybrid power train incorporating hydraulic or electric motors for independent operation and control during vertical phases of flight. This drawing depicts a Coaxial, counter-rotating (CACR) main rotor that can provide torque compensation in the absence of a separate tail rotor or independent thrusters. System components include the following:
 1. Coaxial, Counter-Rotating (CACR) Rotor System (depicted tilted toward viewer for clarity);
 2. Gimballed Rotor Head;

3. Electric Drive "Rotor Motor";
4. "Y" Tail Control Assembly (see Drawing 2);
5. Internal Combustion Engine (ICE);
6. Propeller;
7. Electric Power Supply, comprising a Battery and Electric Power Controller;
8. Landing Gear;
9. Fuselage.

Figure 2:
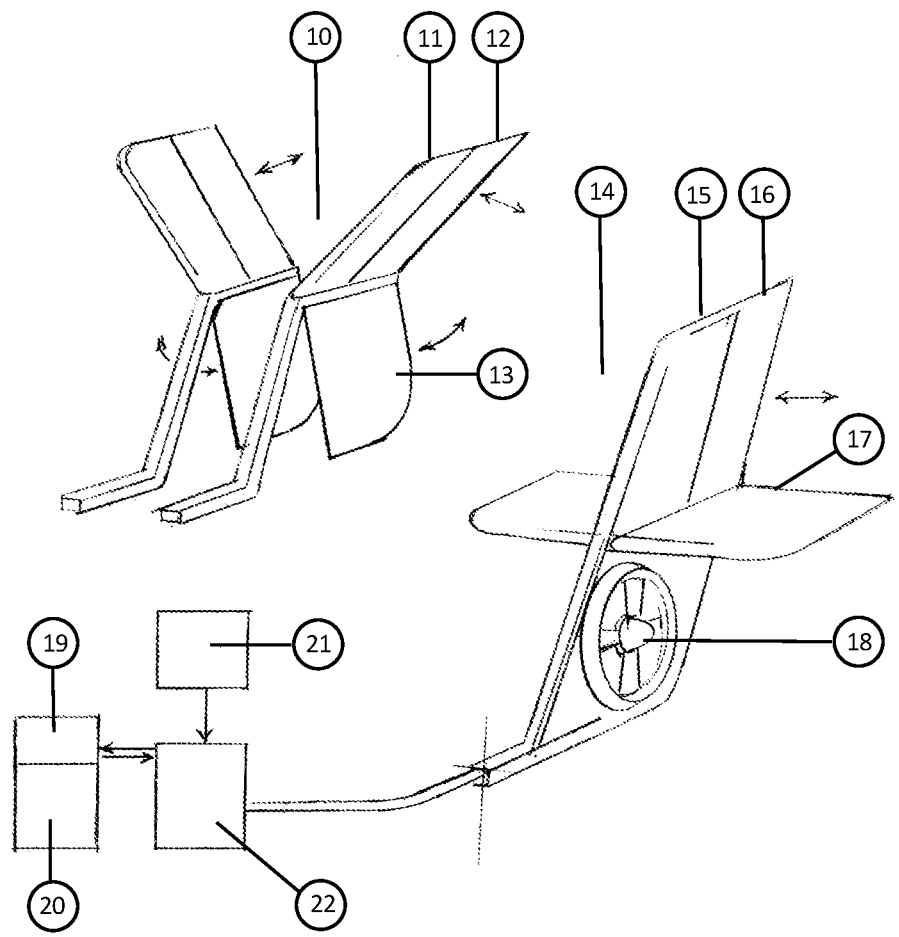
FIG. 2 is a perspective view of alternative tail configurations for the VTOL Gyroplane.

FIG. 2: Alternative Tail Configurations of VTOL Gyroplane:

In a conventional gyroplane, the tail functions in a manner analogous to a fixed wing aircraft, providing vertical and horizontal stabilization, and directional control via a rudder. This drawing depicts two alternative realizations of the required functionality while adding additional capabilities employed during vertical flight. Upper left: a "Y" tail assembly with downwash deflector tabs, suitable for use with a CACR main rotor. Lower right: a conventional cruciform tail assembly, incorporating a ducted fan for torque compensation. System components include the following:

10. "Y" Tail Control Assembly (used with CACR Rotor System);
11. Stabilizers;
12. Ruddervators;
13. Rotor Down-wash Deflector Tabs;
14. "Cruciform" Tail Control Assembly (used with Conventional Rotor System);
15. Vertical Stabilizer;
16. Rudder;
17. Horizontal Stabilizer;
18. Ducted Fan (for Torque Compensation);
19. Gyroscopic Sensor;
20. Torque Compensation Controller;
21. Electric Storage Device (Battery);
22. Electric Power Controller.

Figure 3:
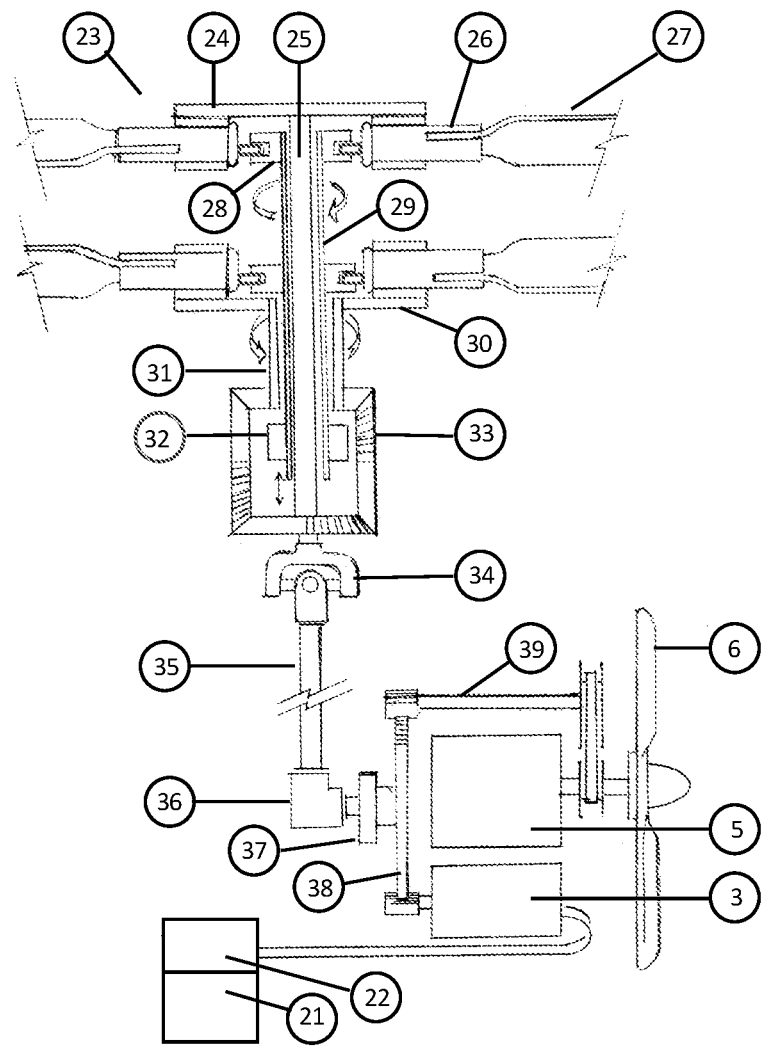
FIG. 3 is a perspective view of the CACR Rotor System and Hybrid Power system for the VTOL Gyroplane.

FIG. 3: CACR Rotor System and Hybrid Power System Detail:

A CACR rotor system is a preferred embodiment of the subject invention, due to the relative simplicity of the mechanism of torque compensation. Although it is possible and potentially useful to drive counter-rotating rotors independently, the use of rotors that are mechanically synchronized allows use of a simpler powertrain and facilitates operation in autorotation. System components include the following:

23. Upper Rotor Assembly of CACR Rotor System;
24. Upper Rotor Head Disk Plate;
25. Upper Rotor Head Drive Shaft;
26. Adjustable Pitch Rotor Spindles (4 or more);
27. Rotor Blades (4 or more);
28. Collective Rotor Pitch Adjustment Spool;
29. Collective Rotor Pitch Adjustment Shaft;
30. Lower Rotor Head Disk Plate;
31. Lower Rotor Head Drive Shaft;
32. Collective Rotor Pitch Adjustment Actuator (Electric, Hydraulic, or Mechanical);
33. Bevel (or Planetary) Gearbox;
34. Universal (or Constant Velocity) Joint;
35. Lower Drive Shaft;
36. 90 Degree Gear Drive;
37. Over-running Clutch;
38. Ring Gear;
39. Power Take-off Drive Shaft;
6. Propeller;
5. Internal Combustion Engine;
3. Electric Rotor Motor;
22. Electric Power Controller;
21. Electric Storage Device (Battery).

A Preferred Embodiment of the Invention Discussed Here Includes

A) Torque compensating main rotor system;
B) Coaxial, Counter-Rotating rotor system;
C) or, a conventional variable pitch rotor with external torque compensation;
D) with common Collective pitch adjustment mechanism;
E) a gimballed main rotor head;
F) A hybrid Power train for transient drive of main rotor system;
G) via, Mechanical or hydraulic systems coupled to prime mover;
H) or, one or more electric motors to drive the main rotor;
I) a Prime Mover, internal combustion engine or turbine;
J) a Propeller for forward flight, driven by prime mover;
K) a Generator and charge control system, driven by prime mover;
L) Electric thruster(s) for torque compensation and/or forward thrust;
M) a Battery system for transiently driving electric motors.

Relationship Between the Components:

The torque compensated main rotor system transiently applies power during vertical flight operations, while operating in autorotation during cruise. Torque compensation is achieved by the use of a coaxial counter-rotating rotor system or by use of a simple variable pitch rotor in conjunction with one or more fixed pitch electric thrusters, positioned to compensate for torque. Fan speed is regulated by electronic sensors and feedback systems. The main rotor provides Collective control of pitch for precise regulation of lift, and a gimballed rotor head for directional control. Hybrid power systems allow precise and potentially automatic control of critical phases of flight including VTOLH. A prime mover driving a propeller meets all power requirements for cruise flight, minimizing required battery weight, and providing long range endurance with simple refueling.

How the Invention Works:

The operational principles, capabilities, advantages and limitations of the helicopter and of the gyroplane are well understood. The objective of this invention is to combine the principal capabilities and advantages of these two aircraft by employing novel solutions for required functional systems.

A torque-compensated main rotor system is designed to be transiently powered for liftoff, landing and hovering (as in a helicopter), while allowing the aircraft to operate in autorotation during cruise, in order to achieve the efficiency, and simplicity of operational and emergency procedures associated with gyroplanes.

In most helicopters, the prime mover (e.g. a piston or turbine engine), directly drives the main rotor in all phases of flight, and the main rotor drives both vertical and horizontal fight, and provides pitch and roll control. Torque compensation is by a variable pitch tail rotor mechanically coupled to the main rotor. In a gyroplane the main rotor is not driven in flight, so the aircraft does not require a tail rotor, instead relying on a rudder for yaw control during a rolling takeoff or in cruise flight.

A Co-Axial, Counter-Rotating (CACR) rotor system provides an alternative solution for a main rotor system, eliminating the need for other systems for torque compensation, although some means for commanding yaw may still be required. It has previously been used in helicopters and has been proposed (but not demonstrated) for use in gyroplanes. Although the advantages of the CACR design are significant, the mechanical design required to implement a helicopter-like Cyclic control function is complex. By eliminating cyclic control in favor of a gimballed rotor head design, it is possible to achieve a simpler system suitable for a light helicopter or gyroplane.

An alternative is to use a conventional variable pitch main rotor, coupled with one or more electrically-driven, fixed-pitch fans for torque compensation and yaw control. A manual or semi-autonomous controller varies fan speed to modulate torque compensation when the main rotor is powered.

Either of these designs provides a solution for torque compensation necessary for powered vertical flight. In the proposed design, Collective pitch adjustment of the main rotor (as in a helicopter) allows fine control of lift for vertical flight without requiring major excursions in engine speed.

A gimballed rotor head provides directional lift, analogous to the Cyclic function of a helicopter, but is simpler and much easier to adapt for a CACR rotor system.

The use of a hybrid power system is useful to optimize the overall performance of the power system given the variation of requirements across a typical flight profile. Application of power to the main rotor system is required for a small fraction of a typical mission: take off, landing and hovering; but requires a substantial fraction of (or may exceed) available power. This can be achieved by mechanical or hydraulic pre-rotation systems but is a natural role for transient electrical power. Such a system also provides a back-up power system for controlled descent in the event of a failure of the prime mover.

The core claims of this patent are: A) to provide a main rotor system that on its own, or in concert with affiliated subsystems, compensates for torque to allow powered vertical flight; and B) a hybrid power system that allows the rotor system to be transiently driven to power vertical takeoff, landing and hovering.

How to Make the Invention:

The invention shares a number of components and subsystems with a helicopter, but is most closely related to a gyroplane.

The invention incorporates an airframe which carries and connects all major components, a fuselage or pod adapted to carry passenger(s) and fuel and provides attachment points for landing gear, an engine to provide horizontal thrust, a tail assembly for directional stability and control, and a mast to carry a main rotor. Most modern gyroplanes also incorporate a pre-rotation system, allowing the rotor to be driven (while on the ground) to a significant fraction of the rotational speed required for liftoff. Because there is no mechanism to compensate for torque associated with the driven rotor, the pre-rotation system must be disengaged before flight.

In order to achieve the objectives of the invention, it is necessary to provide a rotor design or system to compensate for torque, to allow the rotor to be powered during vertical flight or hovering, and a power system to allow the main rotor to be transiently powered during vertical phases of flight. In addition, a system for Collective control of pitch is useful for practical designs.

Replacing a conventional gyroplane rotor (typically 2 blades of fixed pitch) with a variable pitch, co-axial, counter-rotating (CACR) rotor system (consisting of 2 or more rotors, 4 or more blades) is a simple strategy to achieve the objectives of this invention, requiring no other significant alterations to the aircraft. A CACR rotor system satisfying these requirements is described herein.

Alternatively, it is possible to employ a light helicopter rotor, or a conventional gyroplane rotor, modified for collective control of pitch, and adding an electrically powered torque compensating tail fan or multiple peripheral thrusters to achieve the objectives of this invention.

In addition, a system for transiently applying power to the main rotor system during vertical phases of flight is required. This might be a high-performance pre-rotation system driven mechanically or hydraulically by the prime mover, or an independent, electrically powered system.

Essential elements include: A) the variable-pitch, torque-compensating rotor system, and B) the hybrid drive system to allow the rotor system to be powered during vertical phases of flight.

Multiple implementations of each of these essential functional systems are possible and require different subsystems. For example, a CACR main rotor may employ a system of beveled or planetary gears to produce correlated revolution of the counter-rotating blades and to allow the system to be driven from a single source. A single rotor system does not require such a gear system, but does require a sensor-controlled fan for torque compensation.

Other components or subsystems can be used to enhance the performance of the invention, including a centrifugal clutch and/or variable pitch propeller for the primary propulsion system, an over-running (e.g. sprag) clutch for the main rotor, electronic control and stabilization systems for liftoff and landing or automated flight, and systems to allow regeneration of batteries during cruise flight.

Other systems such as folding rotors, hydraulically controlled landing gear, winglets, alternative fuselage designs, or systems to apply power to drive one or more wheels for land transit, may have utility for specific applications, for example enabling a vehicle capable of land or amphibious operations.

The invention is described in terms of functional components or subsystems and similar functions may be achieved with various geometrical configurations, power systems, and auxiliary systems.

How to Use the Invention:

In order to achieve vertical takeoff in the subject invention typical steps include the following:

A) Verify Collective position is full down (low or negative main rotor pitch) to reduce power requirements and prevent unintended liftoff.

B) Start Prime Mover engine and ensure that horizontal drive propeller is disengaged or in low thrust pitch setting.

C) Apply power to main rotor system and spin-up to the RPM range required for flight.

D) Insure that supplemental torque compensation subsystem is operational (if required).

E) Transition main rotor collective pitch to achieve liftoff, while maintaining desired rotor RPM.

F) Hover as desired within constraints of main rotor power.

G) Transition to forward flight by increasing speed and/or pitch of prime mover propeller.

H) Transition to autorotation by adjusting rotor pitch to normal flight position and disk tilt as required.

I) Remove power to main rotor system.

J) Disengage torque compensation system if utilized.

A similar sequence of steps in reverse order is required for vertical descent and landing:

A) Engage torque compensation system if utilized.

B) Apply power to main rotor system.

C) Adjust disk tilt and reduce forward thrust to achieve desired rate of descent.

D) Increase main rotor power and/or rotor blade pitch to arrest descent and achieve hover.

E) Hover as desired within constraints of main rotor power.

F) Transition main rotor collective pitch to achieve desired descent to landing, while maintaining desired rotor RPM.

G) Verify collective position is full down (low or negative main rotor pitch) to prevent unintended liftoff.

H) Turn off prime mover power.

I) Disengage supplemental torque compensation subsystem (if used).

Note that many of the steps associated with vertical flight can be automated, especially if power requirements are satisfied by electrical systems.

Also note that an emergency descent from cruise flight does not require immediate operator intervention, since a gyroplane normally operates in autorotation. The availability of alternative power systems for landing in the event of a prime-mover failure enhances safety and enables automatic procedures.

What is claimed is:

1. A gyroplane, comprising:
an airframe which carries and connects a fuselage or pod adapted to carry passenger(s), mechanisms and systems for control of flight, a fuel tank, a piston or turbine internal combustion engine and a propeller to provide horizontal thrust which together form a prime mover system, a tail assembly to provide directional stability and control, attachment points for landing gear, and a mast to carry a torque-compensated main rotor system; the gyroplane configured to enable vertical takeoff, landing and hovering;
wherein the torque-compensated main rotor system includes one or more rotors, with a common collective pitch control mechanism to allow modulation of lift; and
a hybrid drive system and power train allowing power to be transiently applied to the main rotor system before and/or during vertical phases of flight; while allowing power to be independently controlled and applied by the prime mover system to produce horizontal thrust, in order to achieve aircraft acceleration and to maintain flight, climb or descend, and allow landing, all in the absence of power application to the main rotor system; and
in which the hybrid drive system and power train comprises an electric rotor motor employed to transiently apply power to the main rotor system to provide prerotation of the one or more rotors and during vertical phases of flight.

2. The gyroplane of claim 1, in which the one or more rotors of the torque-compensated main rotor system comprises two or more counter-rotating rotors, offset along the axis of rotation to avoid interference; wherein each rotor includes a plurality of blades extending from a central hub, with the common collective pitch control mechanism to allow modulation of lift; and with a gimballed rotor head, to allow a rotor disk to be physically tilted relative to the gyroplane in order to achieve control of aircraft pitch or roll, or a system for cyclic control of individual ones of the rotor blades to achieve equivalent function without requiring physical tilting of the rotor disk.

3. The gyroplane of claim 1, in which the one or more rotors of the torque-compensated main rotor system comprises a single teetering rotor, with collective pitch control, and with a gimballed rotor head and/or cyclic control mechanism; in which torque compensation is achieved in conjunction with one or more electronically-controlled and driven thruster motors, located on the tail assembly, so that a net resultant thrust is configured to compensate for main rotor torque and/or control yaw; said thruster(s) incorporating one or more of the following accessory structures: a vertical stabilizer, horizontal stabilizer, a perimeter duct, a protective cage, and/or a retractable shroud, to improve safety and/or to enhance aerodynamic performance.

4. The gyroplane of claim 1, in which the one or more rotors of the torque-compensated main rotor system comprises a single teetering rotor, with collective pitch control; and with a gimballed rotor head and/or cyclic control mechanism, in which torque compensation is achieved in conjunction with two or more electronically-controlled and electrically-driven thruster motors located laterally on the airframe, so that differential thrust is configured to compensate for rotor torque and/or control yaw.

5. The gyroplane of claim 4, in which the electronically-controlled and electrically-driven thruster motors located laterally on the airframe, also function to produce supplemental horizontal thrust, in conjunction with the prime mover.

6. The gyroplane of claim 4, in which the electronically-controlled and electrically-driven thruster motors located laterally on the airframe, also function in lieu of the prime mover to produce horizontal thrust.

7. The gyroplane of claim 1, in which the hybrid drive system and power train comprises a battery employed to transiently apply power to the electric rotor motor before and/or during vertical phases of flight, while employing and independently controlling the aforementioned prime mover system to produce horizontal thrust; and with mechanical interconnections to allow the main rotor system to be driven by the prime mover system to recharge the battery in cruise flight, when the electric rotor motor and battery are not used to drive the main rotor system.

8. The gyroplane of claim 1, in which the hybrid drive system and power train comprises a hydraulic motor, pressure reservoir, and pressure generating system driven by the prime mover system, or a mechanical linkage to the prime mover system regulated by a clutch, is employed to transiently apply power to the main rotor system before and/or during vertical phases of flight; and employing a variable pitch propeller, or clutch to control horizontal thrust.

9. The gyroplane of claim 1, configured in which the use of electric motors for lift and for torque compensation allows user-directed or autonomous electronic control of all phases of flight.

10. The gyroplane of claim 4, configured in which the use of electric motors for lift and for torque compensation allows user-directed or autonomous electronic control of all phases of flight.

11. The gyroplane of claim 6, configured in which the use of electric motors for lift, propulsion, and for torque compensation allows-user-directed or autonomous electronic control of all phases of flight.

* * * * *